United States Patent

Konishi et al.

[11] Patent Number: 5,807,951
[45] Date of Patent: Sep. 15, 1998

[54] PHARMACEUTICAL COMPOSITION REGULATING FUNCTION OF A LIVING BODY

[75] Inventors: Jin-emon Konishi, Musashino; Giichi Hamada, Nishinomiya, both of Japan

[73] Assignee: Nippon Zoki Pharmaceutical Co., Ltd., Osaka, Japan

[21] Appl. No.: 841,574

[22] Filed: Apr. 30, 1997

Related U.S. Application Data

[62] Division of Ser. No. 590,509, Jan. 24, 1996, Pat. No. 5,658,896, which is a division of Ser. No. 213,065, Mar. 15, 1994, Pat. No. 5,534,509.

[30] Foreign Application Priority Data

Mar. 19, 1993 [JP] Japan ........................ 5-85322

[51] Int. Cl.$^6$ ............................. A61K 31/80; G08G 1/02
[52] U.S. Cl. ................. 527/300; 106/38.23; 106/38.35; 106/38.51; 106/286.7; 106/600; 106/617; 106/634; 106/656; 423/333; 423/334; 514/63; 514/89; 514/95; 514/99; 514/114; 514/119; 514/120; 514/127; 514/129; 514/210
[58] Field of Search .................... 527/300; 106/38.23, 106/38.35, 38.51, 600, 634, 617, 656, 286.7; 423/333, 334; 514/63, 89, 95, 99, 114, 119, 120, 127, 210; 546/22; 549/6, 218; 558/190, 191, 194, 195, 198; 562/10

[56] References Cited

U.S. PATENT DOCUMENTS

| | | |
|---|---|---|
| 3,959,566 | 5/1976 | Pangonis . |
| 4,036,787 | 7/1977 | Blount . |
| 4,039,474 | 8/1977 | Feistel et al. . |
| 4,056,937 | 11/1977 | Suzuki . |
| 4,089,883 | 5/1978 | Blount . |
| 4,138,421 | 2/1979 | Blount . |
| 4,640,361 | 2/1987 | Smith et al. ............... 106/38.23 |
| 4,863,518 | 9/1989 | Blount . |
| 4,985,254 | 1/1991 | Konishi et al. . |
| 4,985,354 | 1/1991 | Toyomaki et al. . |
| 5,013,558 | 5/1991 | Konishi . |
| 5,057,324 | 10/1991 | Shibayama et al. . |
| 5,127,994 | 7/1992 | Johansson . |
| 5,227,089 | 7/1993 | Hasegawa et al. . |
| 5,523,295 | 6/1996 | Fasman . |
| 5,560,935 | 10/1996 | Konishi et al. . |

FOREIGN PATENT DOCUMENTS

| | | |
|---|---|---|
| 0 341 209 A2 | 11/1989 | European Pat. Off. . |
| 53-101515 | 9/1978 | Japan . |
| 57-77697 | 5/1982 | Japan . |
| 58-35117 | 3/1983 | Japan . |
| 697351 | 9/1953 | United Kingdom . |

OTHER PUBLICATIONS

Yokoi, et al., "Effect of Degree of Polymerization of Silicic Acid on the Gastrointestinal Absorption of Silicate in Rats", *Chem. Pharm. Bull.*, vol. 27, No. 8, 1979, pp. 1733–1739.
Derwent Publications Ltd., London, GB; AN 82–10241J, "Drug For Cultivated Fish", & JP A57183720 (Mitani J.), 12 Nov. 1982, abstract.
"Remedy For Burn", *Patent Abstracts of Japan*, vol. 7, No. 255 (C–189), 6 Oct. 1983, & JPA58121217 (Kagitani Takeo) 19 Jul. 1983, abstract.
"Drug For Food Poisoning", *Patent Abstracts of Japan*, vol. 11, No. 371 (C–462), 3 Dec. 1987 & JPA62145022 (Sofuto Shirika) 29 Jun. 1987, abstract.
"Absorbent For Peroxylipid", *Patent Abstracts of Japan*, vol. 15, No. 474 (C–890), 3 Dec. 1991 & JPA3204803 (Shiseido Co. Ltd.) 6 Sep. 1991, abstract.
*The Merck Index*, Ninth Edition, nos. 7456, 8443, 8232–8243, and 5514–5515 (1976).

*Primary Examiner*—Herbert J. Lilling
*Attorney, Agent, or Firm*—Fisher, Christen & Sabol

[57] ABSTRACT

The present invention provides silicate polymers which regulate the function of a living body by restoring and normalizing the lowered cell functions due to diseases. The silicate polymers are preferably water soluble. The molecular weight of the polymers is in the range of 4,800 to 2,000,000, preferably 20,000 to 1,000,000, and they have a degree of polymerization in the range of 75 to 33,000, preferably 490 to 16,500. The monomer unit is —(SiO$_2$)—. The polymers may be produced by dissolving a water-soluble silicate or a silicic acid containing material such as water glass in water to obtain an aqueous solution. The solution may be admixed with an acid to adjust the pH to 2–10, preferably 4–9.5. A saccharide or sugar alcohol or pharmaceutically acceptable salt may also be admixed with the solution. The aqueous solution is preferably dried to obtain a powder by heating at 150° C. to 250° C. or by lyophilization. The pharmaceutical composition may be used to treat or prevent various diseases, ailments or symptoms associated with allergies, inflammation, or pain.

14 Claims, No Drawings

PHARMACEUTICAL COMPOSITION REGULATING FUNCTION OF A LIVING BODY

This is a divisional of application Ser. No. 08/590,509, filed on Jan. 24, 1996 now U.S. Pat. No. 5,658,896, which is a divisional of application Ser. No. 08/213,065, filed on Mar. 15, 1994, now U.S. Pat. No. 5,534,509.

FIELD OF THE INVENTION

The present invention relates to silicate polymers which regulate physiological functions of a living body, and to a method for manufacturing the silicate polymers. The present invention also relates to pharmaceutical compositions containing said polymer as an active ingredient.

BACKGROUND OF THE INVENTION

A living body maintains its life as an independent organism by controlling physical and chemical conditions of the body within a certain physiological state, and responding to alterations of the internal and external environment.

Such mechanism to maintain homeostasis of a living body is effected by living cells which compose the body, particularly through their cell membranes. The cell membrane, as well known, is made up of a phospholipid bilayer, recognizes various molecules with its surface protein acting as a receptor, and selectively transmits chemicals and ions to achieve intra- and extra-cellular equation or equilibrium of substances and chemical conditions. These mechanisms can provide physiological balance for the cell to act normally.

If said balance was disturbed by any reason, however, various problems may arise. For instance, a change of fatty acid components of phospholipids, i.e. a decrease and increase in the amount of unsaturated and saturated fatty acids, may make the cell membrane solid and lower the fluidity of the membrane.

The alteration of the membrane fluidity may result in hypofunction of membrane receptors as well as of channels for sodium, potassium, calcium and other ions, which eventually brings about functional disturbance of the cell.

The present inventors have conducted continued studies on the substances which enhance the naturally acquired healing power of a living body and contribute to normalization of functions of the body, focusing on the homeostatic mechanisms regulating and restoring neurological, endocrinological and immunological disturbances due to functional abnormality of cells in a morbid state, and, as a result thereof, have accomplished the present invention.

Silicon is a natural element which is widespread in organisms of the animal and plant kingdoms. In particular, it exists as silicate in animal tissues like hair, feather, bone and skin and is known as an essential element in osteogenesis. In animal tissues, it is involved in cross linkage of collagen tissues and is comprised in acidic mucopolysaccharide as one of the components. Silicon is thus an essential element for a living body. It is known, on the other hand, that silicon has pharmacological activities such as immunosuppression through its anti-macrophage activity and antidiabetic activity, when administered to animals.

Some silicates like magnesium silicate and aluminum silicate are widely used as anti-acid pharmaceutical products. However, it has not been reported that a silicate polymer has any specific pharmacological activities.

The present invention relates to water-soluble silicates which are activated by polymerization. It also relates to biologically active substances comprising said silicate polymers which regulate and maintain function of a living body by restoring and normalizing the lowered cell functions due to diseases. It further relates to a pharmaceutical composition containing said silicate polymer as an active ingredient, and to a method for manufacturing thereof.

SUMMARY OF THE INVENTION

The present invention provides novel silicate polymers which regulate the function of a living body, a method for manufacturing thereof and a pharmaceutical composition containing said polymer as an active ingredient. The silicate polymers of the present invention regulate the function of a living body by restoring and normalizing the lowered cell functions due to diseases. The silicate polymers have a molecular weight in the range of 4,800 to 2,000,000, preferably 20,000 to 1,000,000, and a degree of polymerization in the range of 75 to 33,000, preferably 490 to 16,500 wherein the monomer unit is —($SiO_2$)—. The silicate polymers are preferably water-soluble. The polymers of the present invention may be produced by dissolving a water soluble silicate or a silicate acid containing material such as water glass in water to obtain an aqueous solution, and adjusting the pH of the aqueous solution to 2–10, preferably 4–9.5. A saccharide or sugar alcohol or pharmaceutically acceptable salt may be added to the solution. The aqueous solution is preferably dried to obtain a powder by heating at 150° C. to 250° C. or by lyophilization. The pharmaceutical compositions of the present invention comprise a pharmaceutically effective amount of the silicate polymer and may be used to treat or prevent various diseases, ailments or symptoms associated with allergies, inflammation, or pain. The pharmaceutical compositions may be produced in solid, semisolid, liquid or gaseous forms for oral or parenteral administration.

DETAILED DESCRIPTION OF THE INVENTION

The substances of the invention, which regulate the function of a living body by restoring and normalizing lowered cell functions due to diseases, are silicate polymers. The silicate polymers of the invention are polymerized substances of silicic acids or silicates. The polymers are preferably water-soluble silicate polymers. The process of manufacturing the water-soluble silicate polymers may comprise dissolving a silicic acid or a silicate and a saccharide or sugar alcohol in an aqueous solvent to obtain a solution, adjusting the pH of the solution to 4–10, and drying the solution.

The silicic acids which may be used to produce the silicate polymers of the present invention include orthosilicic acid, metasilicic acid, mesodisilicic acid, mesotrisilicic acid, weakly acid substances obtained as gelatinous masses by treating silicates with acids, and mixtures thereof. The silicates which may be used to produce the silicate polymers of the present invention are the salts of silicic acids, for example, salts of silicic acids with alkali metals such as sodium and potassium. Materials containing silicic acid, for instance, water glass which is a concentrated aqueous solution of sodium and other alkali salts of silicic acid, may also be used. Further, a silicate solution prepared by heating and dissolving silicon oxide in alkaline aqueous solution may be utilized. Examples of water-soluble sodium silicates which may be used to produce the silicate polymers of the present invention are sodium metasilicate anhydrous, sodium metasilicate pentahydrate, sodium sesquisilicate, sodium orthosilicate, and mixtures thereof.

The silicate polymers of the invention have a molecular weight in the range of 4,800 to 2,000,000, preferably, 20,000 to 1,000,000, which are determined by gel-filtration, ultrafiltration, electrophoresis and the like. The said silicate polymers have a degree of polymerization in the range of 75 to 33,000, for example 75 to 16,500, preferably 490 to 16,500 wherein the monomer unit is —(SiO$_2$)—.

In embodiments for producing silicate polymers of the present invention a water-soluble silicate such as sodium orthosilicate, sodium metasilicate, potassium orthosilicate or potassium metasilicate, or a silicic acid containing material such as water glass is dissolved in an aqueous solution. Since said aqueous solution of silicate has a high pH value, it is preferable to adjust the solution to pH 2–10, more preferably, pH 4–9.5, by the use of a conventional mineral acid or organic acid such as hydrochloric acid, sulfuric acid or acetic acid. It is desirable to add a saccharide or sugar alcohol such as lactose, mannitol, sorbitol, sucrose, glucose, fructose, galactose, or mixtures thereof to the aqueous solution. A salt such as sodium chloride, potassium chloride, sodium sulfate, or mixtures thereof may also be added to the aqueous solution.

For the purpose of manufacturing a pharmaceutical composition of the invention, said aqueous solution of silicate is preferably dried to a powder. The powderization may be carried out according to a conventional method such as heating or lyophilization. To obtain a preferred powder, for example, the solution is dried by heating at 150° C. to 250° C. Also a conventional lyophilization under reduced pressure may be used to powderize the solution.

To detect the production of silicate polymers, for example, a molybdenum blue coloration is measured. In this technique, a solution of ammonium molybdate is added to the aqueous solution of silicate then sulfite solution is added to produce a blue coloration. The blue coloration is reduced as the polymerization of silicate proceeds. Also, the silicate polymers so produced can be separated by gel-filtration under acidic conditions at high molecular bands. An aliquot of this separated fraction is decomposed under alkali conditions to detect silicate by the molybdenum blue reaction.

Pharmaceutical compositions or preparations comprising the substances of the present invention can be made by combining at least one of the silicate polymers with a suitable carrier or diluent for medical use. The pharmaceuticals or pharmaceutical preparations may be produced by conventional methods provide solid, semisolid, liquid or gaseous forms for oral or parenteral administration.

In manufacturing such preparations, the silicate polymer substances of the present invention may be used either solely or jointly in a form which is suitable for the combination. Also, the substances may be combined with other pharmaceutically active components.

In the case of preparations for oral use, the substances of the present invention may be made into tablets, diluted powders, granules or capsules with or without one or more suitable additives. Exemplary additives which may be used are conventional fillers (e.g. lactose, mannitol, corn starch and potato starch), binders (e.g. crystalline cellulose, cellulose derivatives, gum arabic, corn starch and gelatin), lubricants (e.g. talc and magnesium stearate), extenders, moisturizers, preservatives, perfumes, and mixtures thereof.

In other embodiments, the polymeric silicate substances of the present invention may be mixed with at least one base material. The base material may be an oleaginous composition or fat/oil type material (e.g. cacao butter), an emulsifying base material, a water-soluble base material (e.g. Macrogol) or a hydrophilic base material, etc., to obtain a suppository.

In the case of injections, the silicate polymer substances may be made into a solution or a suspension in aqueous solvents or nonaqueous solvents such as distilled water for injection, physiological saline liquid, Ringer solution, plant oil, synthetic fatty acid glycerides, higher fatty acid esters, propylene glycol, and mixtures thereof.

Further, depending upon the state of the patient, or the type of the disease, the substances may be made into other preparation forms such as ointments and eye drops which are most suitable for the therapy.

A desired dose of the silicate polymer substances of the present invention may vary depending upon the patent to be treated, preparation form, method of administration, period for administration, etc. In general 1 μg/kg to 10 mg/kg per day may be given to an adult for achieving the desired pharmaceutical effect.

In the case of parenteral administration such as injections, the desired dose may be ⅓ to ¹⁄₁₀ as large as an oral dose in general because of the difference of absorption.

The following examples illustrate the present invention wherein all parts, percentages, ratios, and amounts are by weight and all temperatures are in °C. unless otherwise indicated:

EXAMPLE 1

7.6 g of water glass (silicon; 1.2 g) was dissolved in 100 ml of water. 97.5 g of lactose was dissolved in 300 ml of water with heating. The water glass solution was mixed with the lactose solution, and then the pH was adjusted to 8.0 with diluted hydrochloric acid. The reaction mixture was dried at 200° C. to obtain 90 g of a powder. The resulting silicate polymers of the present invention have the following physical properties and contain 12 mg of silicon per 1 g of polymer:

Molecular weight: 13,000 to 1,000,000

Degree of polymerization: 210 to 16,500

EXAMPLE 2

12.9 g of sodium metasilicate (silicon; 1.2g) was dissolved in 100 ml of water. 95.8 g of lactose was dissolved in 300 ml of water with heating. The aqueous solution of sodium metasilicate was mixed with the lactose solution, and then the pH was adjusted to 8.0 with diluted hydrochloric acid. The reaction mixture was dried at 200° C. to obtain 90 g of a powder. The resulting silicate polymers of the present invention have the following physical properties and contain 12 mg of silicon per 1 g of polymer:

Molecular weight: 15,000 to 900,000

Degree of polymerization: 250 to 15,000

EXAMPLE 3

5.9 g of sodium orthosilicate (silicon; 0.6 g) was dissolved in 100 ml of water. 99 g of mannitol was dissolved in 300 ml of water with heating. The aqueous solution of sodium orthosilicate was mixed with the mannitol solution, and then the pH was adjusted to 8.0 with diluted hydrochloric acid. The reaction mixture was dried at 200° C. to obtain 88 g of a powder. The resulting silicate polymers of the present invention have the following physical properties and contain 6 mg of silicon per 1 g of polymer:

Molecular weight: 20,000 to 1,000,000

Degree of polymerization: 330 to 16,500

EXAMPLE 4

1.89 g of water glass (silicon; 0.3g) was dissolved in 100 ml of water. 500 ml of 20% aqueous solution of lactose was added thereto, and then the pH was adjusted to 8.0 with diluted hydrochloric acid. Each 1.2 ml of the solution was pipetted into a vial and lyophilized. The resulting dry-powdered silicate polymers of this invention have the following physical properties and contain 0.6 mg of silicon per vial:

Molecular weight: 30,000 to 1,500,000

Degree of polymerization: 490 to 25,000

EXAMPLE 5

In the following experiments, the amount of the silicate polymer substance of the present invention is indicated as the amount of silicon (Si) contained therein, such as Si g/ml or Si mg/kg:

Experiment 1. Inhibitory effect on mast cell degranulation:

An inhibitory effect of a substance of the invention on mast cell degranulation was determined according to a conventional method. A solution of the substance was added to a cell suspension of rat peritoneal mast calls and incubated at 37° C. for 10 minutes. To this cell suspension, a solution of Compound 48/80, a histamine releaser, was added. The reaction mixture was incubated for 10 minutes, and then the reaction was stopped by adding a cold buffer solution. The supernatant was separated by centrifugation, and the amount of histamine in it was measured fluorometrically. The inhibition rate of the substance on histamine release was determined according to a conventional method. The substance significantly inhibited the histamine release from mast cells.

An example of the results is shown in Table 1:

TABLE 1

| Concentration of the substance of Example 1 (Si g/ml) | Inhibition rate on histamine release (%) |
| --- | --- |
| $1 \times 10^{-8}$ | $6.2 \pm 2.0$ |
| $1 \times 10^{-7}$ | $7.6 \pm 8.5$ |
| $1 \times 10^{-6}$ | $37.6 \pm 0.7$ |
| $1 \times 10^{-5}$ | $83.0 \pm 11.9$ |
| $1 \times 10^{-4}$ | $96.2 \pm 0.9$ |

Experiment 2. Inhibitory effect on histamine release by antigen-antibody reaction:

Rats were passively sensitized by intraperitoneal injection of anti-ovalbumin serum (IgE-like antibody). Twenty-four hours thereafter, a suspension of peritoneal mast cells of the rats was prepared. To this cell suspension, a solution of a polymer substance of the invention was added, and incubated for 10 minutes at 37° C. A solution of ovalbumin was then added to the mixture to induce an antigen-antibody reaction for 10 minutes. The reaction was stopped and the inhibition rate of histamine release by the substance was measured, according to the methods described above in Experiment 1. The substance significantly inhibited the histamine release from mast cells caused by antigen-antibody reaction.

An example of the results is shown in Table 2:

TABLE 2

| Concentration of the substance of Example 1 (Si g/ml) | Inhibition rate on histamine release (%) |
| --- | --- |
| $1 \times 10^{-8}$ | $3.1 \pm 1.1$ |
| $1 \times 10^{-7}$ | $16.6 \pm 12.2$ |
| $1 \times 10^{-6}$ | $85.1 \pm 5.9$ |
| $1 \times 10^{-5}$ | $96.5 \pm 4.5$ |
| $1 \times 10^{-4}$ | $98.4 \pm 2.8$ |

Experiment 3. Inhibitory effect on hyaluronidase activity:

A substance of the present invention was added to a solution containing hyaluronidase, and incubated at 37° C. for 10 minutes. A solution of hyaluronic acid as a substrate was added to the solution to react with the enzyme for 15 minutes, and then the reaction was terminated by addition of a succinic acid-buffer solution. The absorbance of the reaction solution at 540 nm was measured. The inhibition rate of the substance to hyaluronidase was calculated in comparison with the absorbance of a control solution wherein a physiological saline solution was used instead of the tested substance. The substance showed inhibition of hyaluronidase activity dose-dependently.

An example of the results is shown in Table 3:

TABLE 3

| Concentration of the substance of Example 2 (Si µg/ml) | Inhibition rate to hyaluronidase (%) |
| --- | --- |
| 50 | 10.9 |
| 100 | 24.5 |
| 250 | 51.7 |
| 500 | 89.1 |

Experiment 4. Inhibitory effect on vascular permeability:

Guinea pig nasal cavity was perfused with histamine solution, and the increase of nasal membrane permeability and of nasal secretion was investigated by measuring the amount of dye extravasated at the site according to the method of Kojima and Tsutsumi [Allercy, vol. 35, 180–187 (1986)]. A polyethylene tube was inserted to the nasal cavity from an incised trachea for perfusion, and a solution of dye was intravenously injected. A physiological saline solution was perused at 1 ml per minute. The initial perfusate for 10 minutes was drained off from the nostrils for washing, and the perfusate of the following 20 minutes was collected (Perfusate A). A physiological saline solution containing histamine was then perfused for 10 minutes to collect the perfusate (Perfusate B). A normal saline solution was again perfused for 10 minutes to collect the perfusate (Perfusate C). Each perfusate was centrifuged and the absorbance of the supematant was measured at 620 nm.

A polymer substance of the invention, which was intraperitoneally administered 30 minutes before histamine perfusion, significantly suppressed the permeability of the nasal membrane for the dye.

An example of the results is shown in Table 4 where the amount of dye in the perfusate is expressed as the absorbance:

TABLE 4

| | Amount of dye in the perfusate | | |
| --- | --- | --- | --- |
| | | Dose of the substance of Exampe 2 (Si mg/kg) | |
| Perfusate | Saline | 12.5 | 25.0 |
| A | $0.88 \pm 0.44$ | $0.45 \pm 0.13$ | $0.33 \pm 0.09$ |
| B | $4.07 \pm 2.40$ | $1.34 \pm 1.12$ | $0.75 \pm 0.46$ |
| C | $3.82 \pm 2.05$ | $1.72 \pm 1.75$ | $0.88 \pm 0.56$ |

Experiment 5. Effect on disturbance of peripheral blood circulation:

The effect of a substance of the invention on the disturbance of peripheral blood circulation was determined, as an index of improving paresthesia. Quinoform was administered to rats intraperitoneally for 27 days in progressively increasing amounts to cause disturbance of peripheral circulation. The hind limbs of the quinoform-treated rat were then exposed to cold water of 5° C. for 2 minutes. The effectiveness of the substance in improving peripheral blood circulation was evaluated by monitoring the recovery process of the limb temperature using thermographical image analysis. The substance was intravenously administered to rats consecutively for 7 days from the 21st day of quinoform treatment.

An example of the results is shown in Table 5 where the dose of the substance is shown in parentheses (Si mg/kg):

TABLE 5

| | Average skin temperature (°C.) of the hind limb at 15 minutes ater exposure to cold water |
|---|---|
| Untreated group | 27.1 ± 0.7 |
| Control: quinoform-treated | 23.9 ± 0.5 |
| The substance of Example 1 | |
| (5) | 24.2 ± 0.2 |
| (10) | 26.3 ± 0.2 |
| (20) | 27.0 ± 0.3 |

Experiment 6. Analgesic effect:

The analgesic effects of the silicate polymer of Example 3 were studied by the Randall-Selitto method using SART-stressed mice prepared according to Kita, et al. [Folia Pharmacol. Jap.: vol. 71, 195–210 (1975)]. The SART-stressed animal is an animal model of hyperalgesia, with at lowered threshold to pain sensation. It is highly responsive when applying pressure stimulus to the tail root of the animal with the Randall-Selitto device.

The effect of the polymeric substance was evaluated by an analgesic index: the quotient of the pain threshold after treatment divided by that before treatment. The lowered pain threshold of SART-stressed mice was elevated dose-dependently up to the normal level, when the polymeric substance of the present invention was intraperitoneally administered.

An example of the results is shown in Table 6:

TABLE 6

| Dose of the substance of Example 3 (Si mg/kg) | Average pain threshold |
|---|---|
| 2.5 | 1.35 |
| 5.0 | 1.51 |
| 10.0 | 1.70 |

Experiment 7. Acute toxicity:

Acute toxicity of the silicate polymer of Example 3 of the present invention was measured by administering the substance intravenously or intraperitoneally to a group of 10 ddY male mice. The $LD_{50}$ values of the substance were 60.4 Si mg/kg (i.v.) and 71.8 Si mg/kg (i.p.), respectively.

As shown by the above-mentioned results of the pharmacological studies, the silicate polymers of the present invention have biological activities which restore and normalize the abnormal functions of a living body due to diseases. For example, the silicate polymer substances of this invention show a therapeutic effect on diseased conditions such as allergy or inflammation, and elevate the lowered pain threshold in animals under stress.

The substances of the present invention have, as demonstrated, an effect on neurological, endocrinological and immunological systems and show excellent activity for restoring and normalizing the impaired functions of the living body due to diseases. They are very useful as a drug such as an anti-allergic agent, ant-inflammatory agent, improving agents for peripheral blood circulation and paresthesia, and analgesic agents. Consequently, a pharmaceutical composition containing a silicate polymer of the invention as an active ingredient is useful for treating or preventing various diseases accompanied by or associated with allergy, inflammation or pain, including bronchial asthma, pollinosis, allergic rhinitis, urticaria, eczema, contact dermatitis, allergic conjunctivitis, gastritis, peptic ulcer, enterocolitis, idiopathic ulcerative colitis, rheumatoid arthritis, herpes, systemic lupus erythematosus, gastrointestinal neurosis, autonomic dystonia, vertigo, neuralgia, frozen shoulder, lower back pain, headache, etc.

EXAMPLE 6

Some prescriptions of pharmaceutical compositions which contain the substances of the present invention as active ingredients are shown below as examples. These examples, however, do not limit the present invention:

Prescription example 1 (tablet)

| Component | Content in a tablet (mg) |
|---|---|
| silicate polymer of this invention | 100 |
| lactose | 58 |
| crystalline cellulose | 40 |
| magnesium stearate | 2 |
| Total | 200 |

Prescription example 2 (capsule)

| Component | Content in a capsule (mg) |
|---|---|
| silicate polymer of this invention | 50 |
| lactose | 78 |
| potato starch | 15 |
| magnesium stearate | 2 |
| talc | 5 |
| Total | 150 |

Prescription example 3 (injection)

| Component | Content in an ampule (mg) |
|---|---|
| silicate polymer of this invention | 10 |
| saline | proper amount |
| Total | 1 ml |

Prescription example 4 (ointment)

| Component | (g) |
|---|---|
| silicate polymer of this invention | 1 |
| glycerol monostearate | 5 |
| white vaseline | 94 |
| Total | 100 |

Prescription example 5 (suppository)

| Component | (g) |
|---|---|
| silicate polymer of this invention | 0.1 |
| witepsol H-15 (hard fat) | 1.9 |
| Total | 2.0 |

What is claimed is:

1. A process for manufacturing a water-soluble silicate polymer comprising dissolving a silicic acid or a silicate and a saccharide or sugar alcohol in an aqueous solvent to obtain a solution, adjusting the pH of the solution to 4–10, and drying the solution.

2. A process as claimed in claim 1 wherein the water soluble silicate polymer has a molecular weight in the range of 4,800 to 2,000,000 as determined by gel-filtration.

3. A process as claimed in claim 2 wherein the water soluble silicate polymer has a degree of polymerization in the range of 75 to 33,000 wherein the monomer unit is —($SiO_2$)—.

4. A process as claimed in claim 1 wherein the silicate is water-soluble silicates.

5. A process as claimed in claim 4 wherein the water-soluble silicates are salts of silicic acid with alkali metals.

6. A process as claimed in claim 5 wherein the silicates are sodium silicates.

7. A process as claimed in claim 4 wherein the water-soluble silicates are water glass.

8. A process as claimed in claim 1 wherein a saccharide is dissolved to obtain said solution.

9. A process as claimed in claim 8 wherein the saccharide is lactose.

10. A process as claimed in claim 1 wherein the aqueous solution is dried to a powder.

11. A process as claimed in claim 10 wherein the drying method is lyophilization.

12. A process as claimed in claim 1 wherein said drying is by heating the solution at a temperature of 150° C. to 250° C.

13. A process as claimed in claim 1 wherein the pH is adjusted with a mineral acid or an organic acid.

14. A process as claimed in claim 13 wherein the acid is hydrochloric acid, sulfuric acid, or acetic acid.

* * * * *